United States Patent [19]

Laabs et al.

[11] Patent Number: 5,542,929
[45] Date of Patent: Aug. 6, 1996

[54] SUCTION DEVICE FOR MEDICAL USE

[76] Inventors: Walter Laabs, Oestringer Str. 64, 2948 Grafschaft-Schortens; Hans-Günter Appel, Auenweg 2, 2948 Accum 1., both of Germany

[21] Appl. No.: 341,034

[22] Filed: Nov. 15, 1994

Related U.S. Application Data

[63] Continuation of Ser. No. 73,617, Jun. 8, 1993, abandoned, which is a continuation of Ser. No. 645,887, Jan. 25, 1991, abandoned.

[30] Foreign Application Priority Data

Jan. 27, 1990 [DE] Germany ............... 40 02 373.7

[51] Int. Cl.⁶ ............................................. A61M 1/00
[52] U.S. Cl. .................. 604/119; 604/902; 604/129
[58] Field of Search ................. 604/117, 118, 604/119, 114, 19, 902, 244; 606/123, 191, 192, 194

[56] References Cited

U.S. PATENT DOCUMENTS

| | | | |
|---|---|---|---|
| 2,945,496 | 7/1960 | Fosdal | 604/115 |
| 3,690,315 | 9/1972 | Chittenden et al. | 604/129 |
| 3,810,471 | 5/1974 | Truhan | 604/902 |
| 4,356,823 | 11/1982 | Jackson | 604/119 |
| 4,610,664 | 9/1986 | Harle | 604/119 |
| 4,648,871 | 3/1987 | Jacob | 604/902 |
| 4,787,599 | 11/1988 | Nyboer | 604/902 |
| 4,792,328 | 12/1988 | Beck et al. | 604/131 |
| 4,857,047 | 8/1989 | Amoils | 604/119 |
| 4,867,747 | 9/1989 | Yarger | 604/902 |
| 4,878,900 | 11/1989 | Sundt | 604/119 |
| 4,966,584 | 10/1990 | Nguyen | 604/902 |
| 5,013,300 | 5/1991 | Williams | 604/119 |
| 5,120,316 | 6/1992 | Morales et al. | 604/244 |
| 5,171,222 | 12/1992 | Euteneuer et al. | 606/194 |
| 5,329,921 | 7/1994 | Socaris et al. | 604/244 |
| 5,334,147 | 8/1994 | Johnson et al. | 604/96 |

FOREIGN PATENT DOCUMENTS

| | | |
|---|---|---|
| 0251694 | 1/1988 | European Pat. Off. . |
| WO83/02900 | 9/1983 | WIPO . |

*Primary Examiner*—C. Fred Rosenbaum
*Assistant Examiner*—Chalin Smith
*Attorney, Agent, or Firm*—Cushman Darby & Cushman, L.L.P.

[57] ABSTRACT

The invention relates to a suction device for medical use, in which an aspirator (1) as illustrated in FIG. 1 is proposed, which has one or a plurality of side openings (3), and which is provided with a valve (4) which responds to underpressure.

3 Claims, 1 Drawing Sheet

SUCTION DEVICE FOR MEDICAL USE

This is a continuation of application Ser. No. 8/073,617, filed on Jun. 8, 1993, which was abandoned upon the filing hereof, which is a continuation of Ser. No. 07/645,887, filed Jan. 25, 1991, abandoned.

The invention relates to suction devices for medical use, such as are employed in surgery, dentistry and in intensive care units.

In the course of performing an operation it is necessary to remove flowing blood, tissue fluid, tissue fragments, bone splinters and bone meal as well as pus from the site of the operation. Added to this is that the customary rinsing fluids, such as saline or Ringer's solution, must be constantly replaced and therefore also removed. Formerly cotton swabs were used for this, while today suction devices are employed. In dentistry, for example, it is necessary to suck off sputum, blood and drilling residue. In connection with intensive care, anesthesia and endoscopy it is necessary to aspirate body fluids of different viscosity and composition (for example, mucus, blood, urine, feces, bile, gastric juices, etc., and also contrast fluids). Suction devices of this type consist of a fixedly installed or mobile vacuum pump connected to an underpressure collecting container which, in turn, is connected with a so-called secretion bottle via an overflow protector, which again in turn is connected with the suction tip by means of a suction hose. There are aspirators with small and with large passages, where aspirators with large passages are considered to be those with an interior diameter larger than 4.9 mm. These aspirators may be made of plastic, but also of metal or other materials.

If in the course of aspiration tissue completely covers the suction tip of the aspirator, underpressure is created which can reach close to the pump underpressure of 0.1 bar. Because of this, tissue is forced into the suction opening by air pressure, so that tissue damage may occur. It is also possible that tissue is sliced off by the inner edge of the suction opening, which also may lead to injury.

To prevent adherence of the suction tip on tissue, so-called atraumatic aspirators have been developed in the meantime, where side openings are present above the suction tip, through which it is possible to aspirate additional air. Although this results in a reduction of the suction output, the critical underpressure in the suction tip and thus injury to or aspiration of tissue is avoided or reduced. To keep a reduction of the suction output as small as possible, aspirators with so-called vacuum controls have already been developed, which have a lateral opening which must be covered with a finger in the manner of a flute during aspiration and where the underpressure in the tissue can be reduced by uncovering the opening. But the vacuum control must be performed by hand, for which reason such aspirators must be watched during manipulation and therefore can be disruptive during an operation.

It has also been found that the so-called atraumatic aspirators, in which air flow from the lateral bores mixes with the main flow of air, result in a very disturbing output of noise. These aspirators function in accordance with the principle of a recorder and the noises are created, as long as there is no aspiration, by the swirling of the side air in the main air flow. Loudness is determined by the speed of the air in the hose and by resonating oscillations of the aspirator; the frequency of these noises is a function of the shape and location of the lateral bores. The whistling sounds generated in this way interrupt the concentration of the operating team and can be quite annoying during long-lasting operations.

For these reasons there is a requirement for suction devices of the type described above which do not act in a traumatizing way and also do not result in undesired noise generation.

It is the object of the invention to propose suction devices with aspirators with one or a plurality of side openings which are characterized in that they are provided with a valve which responds to underpressure.

It has been surprisingly found that it is possible to obtain the advantages of atraumatic aspirators while, at the same time, preventing undesirable noise generation and increasing suction output, by providing the lateral openings with a valve which responds to underpressure. Such valves may be, for example, slit valves, flap valves or ball valves. It has been found that the desired effect can be attained in the simplest and most cost-effective way in that the aspirator is provided with one or a plurality of oblong holes, which are covered with a thin, slit or slittable foil. When the suction device has been connected in the customary manner to the vacuum pump, but aspirating does not take place, the difference in air pressure is sufficient to keep this slit valve closed and in this way to prevent the entry of side air and thus the generation of noise. However, at the moment when tissue closes off the suction opening and critical underpressure begins to build up in the aspirator, side air can enter through the slit valve, so that the underpressure is lowered to a value at which no damage to the tissue is caused. But this only reduces the suction output by a little.

If the suction device is made of plastic, the covering of the oblong hole(s) can already take place in a manner known per se in the course of manufacture by injection molding or extrusion. Extruded aspirators may be provided with one or a plurality of grooves over their entire length on the inside (FIG. 3) or outside (FIG. 4), so that a layer of wall of the thickness of a membrane remains. This groove replaces the oblong hole. The groove can be slitted in as many places as desired. However, it is also possible that, as in the case of the suction devices made of metal, a thin foil is glued over the oblong hole or that a fixed, very thin hose with a slit is pushed over it. It is even possible to glue a foil over the oblong hole or to push a hose over it, which does not yet have a slit but can be easily slit, so that the surgeon can make the slit himself in the course of the operation by simply cutting the foil or the hose. In this case the desired underpressure can be regulated by the adjustable position of the valve slit.

The use of metal instruments instead of disposable plastic items has the advantage that because of their simple construction these aspirators can be easily cleaned and sterilized, so that not only money can be saved, but the amount of waste can also be reduced.

As a rule, the oblong holes or side openings and their valves should be at a great distance from the suction tip, because in this way it is possible to assure that the valves remain functional during insertion. However, in case of deep operation sites, for example the abdominal cavity, it is advantageous to provide a plurality of valve openings over the entire length of the aspirator. If suction openings are blocked by soft tissue, for example, other valve openings can maintain the suction effect in the liquid.

The invention will be described in detail by means of the drawings.

Figure 1:
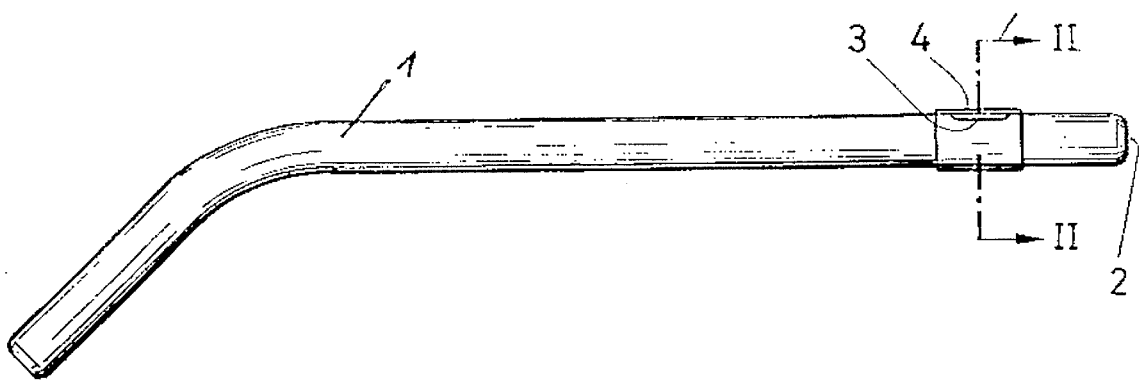
FIG. 1 is a lateral view of the aspirator in accordance with the invention.
Figure 2:
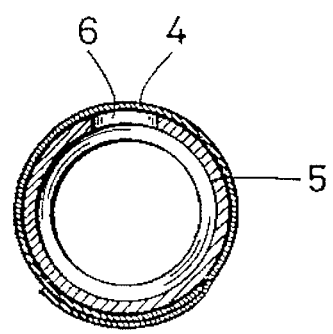
FIG. 2 is a cross sectional view of the same aspirator.
Figure 3:
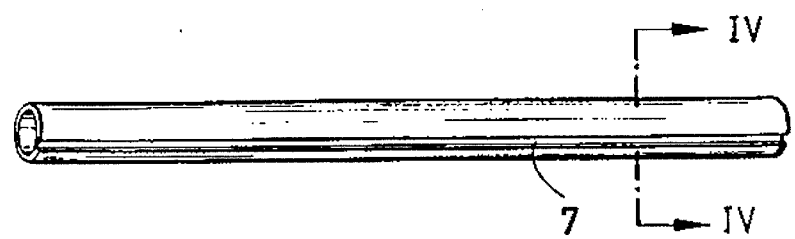
FIG. 3 shows the aspirator with an extruded groove.

The aspirator (1) has an opening (2) and one or a plurality of oblong holes (3), which in turn are covered with a foil (4) which is already slitted or can be slitted. It can be seen in the cross sectional view that the wall (5) of the aspirator (1) is covered in the area of the oblong hole (3) by the foil (4) with the slit (6). The foil used for the cover can, for example, either be injection molded or extruded during manufacture or it can later be pulled in the shape of a hose over the oblong hole or glued over it in the shape of an adhesive foil.

Figure 4:
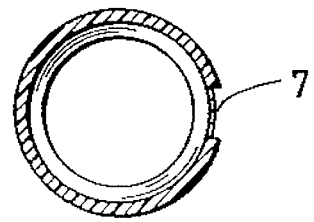
FIG. 4 is a cross sectional view of the aspirator in accordance with FIG. 3.

If made from plastic, the aspirator (1) can also be provided with a groove (7) of considerably thinner wall thickness, as shown in detail in FIG. 4. This groove can be slitted at any desired length.

We claim:

1. A suction device for medical use, comprising:

an aspirator comprising a tube having a circumference and provided with at least one side opening, said aspirator having an open suction end at one end of said tube through which matter may enter and a hose end for attachment to a suction device; and a foil covering said side opening, said foil having a slit therein having a thickness such that said foil is openable in response to a pressure differential thereacross, said open suction end being free of any obstruction and said at least one side opening being spaced along said tube a distance from said open suction end and said hose end.

2. The suction device of claim 1, wherein the at least one side opening is disposed at the suction end of the aspirator conduit.

3. The suction device of claim 1, wherein the at least one side opening is disposed at the hose end of the aspirator conduit.

* * * * *